US007924308B2

(12) United States Patent
Abe et al.

(10) Patent No.: US 7,924,308 B2
(45) Date of Patent: Apr. 12, 2011

(54) ELECTRONIC ENDOSCOPE APPARATUS AND METHOD OF CONTROLLING IMAGE LUMINANCE FOR ELECTRONIC ENDOSCOPE APPARATUS

(75) Inventors: Kazunori Abe, Saitama (JP); Yoshifumi Donomae, Kawasaki (JP)

(73) Assignee: FUJIFILM Corporation, Tokyo (JP)

( * ) Notice: Subject to any disclaimer, the term of this patent is extended or adjusted under 35 U.S.C. 154(b) by 1543 days.

(21) Appl. No.: 11/253,630

(22) Filed: Oct. 20, 2005

(65) Prior Publication Data
US 2006/0082646 A1 Apr. 20, 2006

(30) Foreign Application Priority Data

Oct. 20, 2004 (JP) .................................. 2004-305040

(51) Int. Cl.
*A61B 1/04* (2006.01)
(52) U.S. Cl. .......... 348/68; 358/474; 358/471; 358/482; 382/274; 382/254; 600/180; 600/113; 348/71; 348/241
(58) Field of Classification Search .................. 358/483, 358/482, 471, 473, 501, 505.474; 348/71, 348/68, 76, 241, 65; 600/180, 113, 160
See application file for complete search history.

(56) References Cited

U.S. PATENT DOCUMENTS

| 5,515,449 | A  | * | 5/1996  | Tsuruoka et al. | 382/128 |
| 5,956,416 | A  | * | 9/1999  | Tsuruoka et al. | 382/128 |
| 6,081,371 | A  | * | 6/2000  | Shioda et al.   | 359/372 |
| 6,456,317 | B1 | * | 9/2002  | Matsumoto et al.| 348/68  |
| 6,545,703 | B1 | * | 4/2003  | Takahashi et al.| 348/69  |
| 6,724,418 | B1 | * | 4/2004  | Takahashi       | 348/65  |
| 6,748,109 | B1 |   | 6/2004  | Yamaguchi       |         |
| 6,956,418 | B2 | * | 10/2005 | Kwak et al.     | 327/158 |
| 7,432,961 | B2 | * | 10/2008 | Takeshita       | 348/227.1 |
| 2004/0044275 | A1 | * | 3/2004 | Hakamata      | 600/310 |
| 2004/0212808 | A1 |   | 10/2004 | Okawa et al. |         |
| 2005/0012831 | A1 | * | 1/2005 | Yano          | 348/234 |
| 2005/0222500 | A1 | * | 10/2005 | Itoi         | 600/180 |
| 2006/0082646 | A1 | * | 4/2006 | Abe et al.    | 348/68  |
| 2009/0290018 | A1 | * | 11/2009 | Abe          | 348/76  |

FOREIGN PATENT DOCUMENTS

| JP | 62-155689    | 7/1987 |
| JP | 06-078312 A  | 3/1994 |
| JP | 2000-083172  | 3/2000 |
| JP | 2003-250761 A| 9/2003 |
| JP | 2004-112487  | 4/2004 |

OTHER PUBLICATIONS

Japanese Abstract No. 06078312, dated Mar. 18, 1994.
Japanese Abstract No. 2002058639, dated Feb. 26, 2002.
Japanese Office Action, dated Mar. 16, 2010.

* cited by examiner

*Primary Examiner* — Negussie Worku
(74) *Attorney, Agent, or Firm* — Sughrue Mion, PLLC

(57) ABSTRACT

An image obtained by an electronic endoscope apparatus is changed to an image that is appropriate for observation with suppressed halation and fewer dark areas. Halation detection means detects halation of a predetermined level or higher in an image represented by a signal obtained by an imaging device, based on the signal. Light amount adjustment means decreases an amount of light emitted from illumination means to cause the halation to become a predetermined level or lower. Luminance conversion means processes the signal so as to generate a luminance conversion image wherein only a dark area having a predetermined luminance or lower in the image due to the decrease in the amount of the light is changed to have a higher luminance.

4 Claims, 3 Drawing Sheets

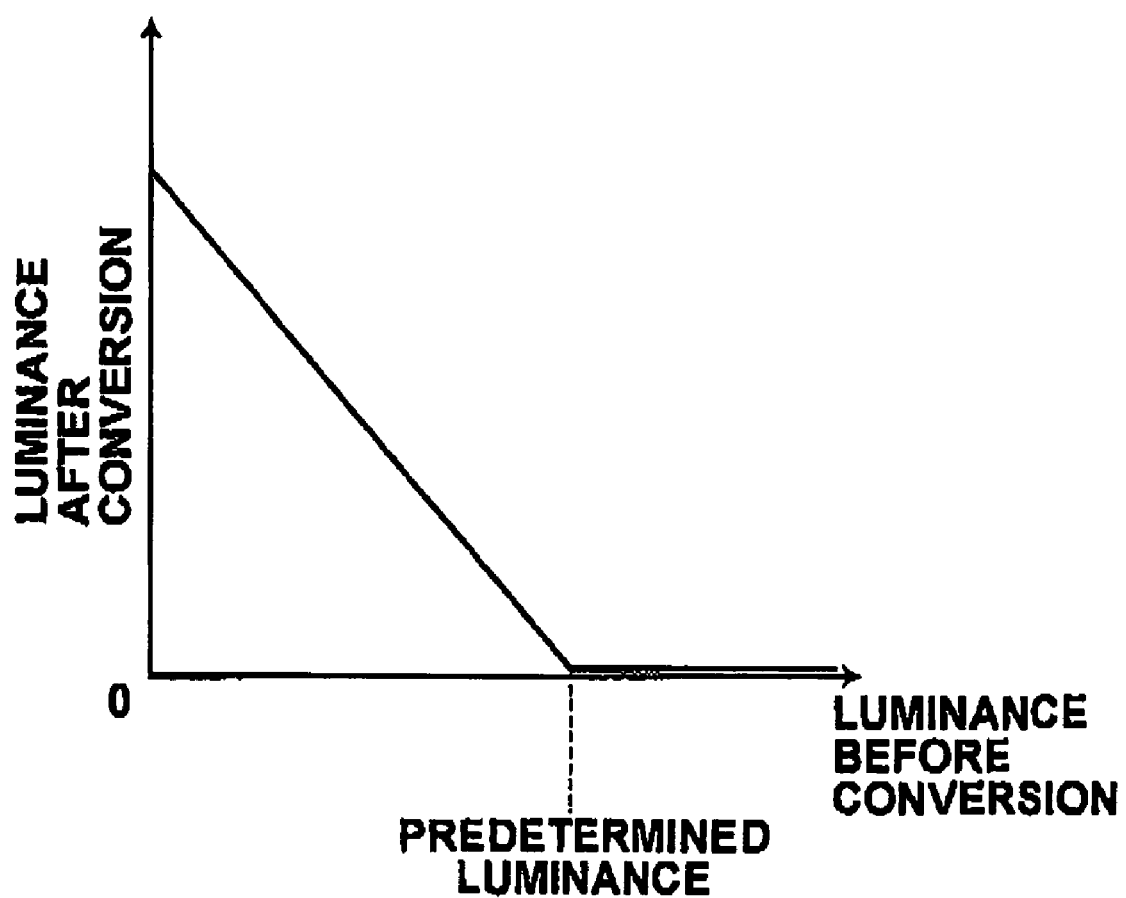

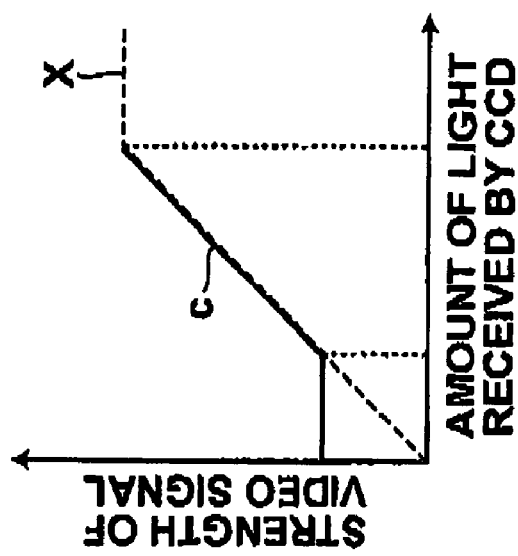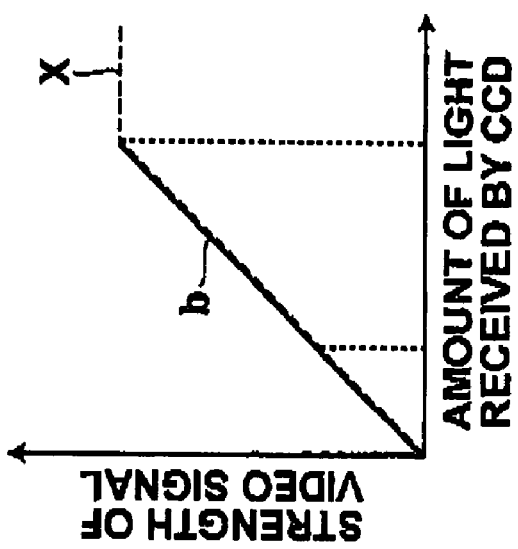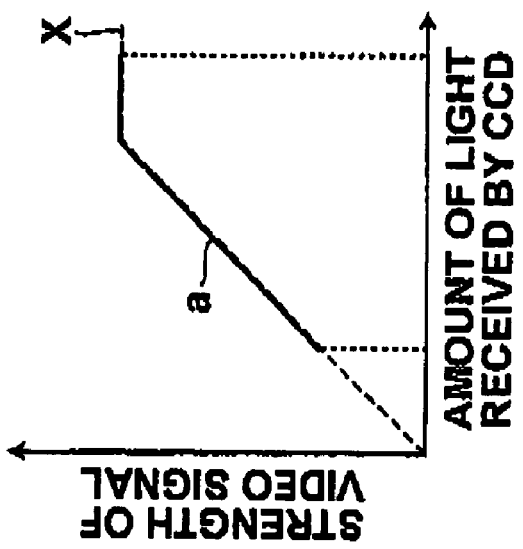

ELECTRONIC ENDOSCOPE APPARATUS AND METHOD OF CONTROLLING IMAGE LUMINANCE FOR ELECTRONIC ENDOSCOPE APPARATUS

BACKGROUND OF THE INVENTION

1. Field of the Invention

The present invention relates to an electronic endoscope apparatus. More specifically, the present invention relates to control for improving quality of an image obtained by an electronic endoscope apparatus.

2. Description of the Related Art

When an observation target is viewed with use of an electronic endoscope apparatus, a part of the observation target near an illumination (a light emission part) of a scope of the endoscope apparatus reflects more light. Consequently, halation tends to occur in the part in an image obtained by the endoscope apparatus, because an amount of light received by an imaging device such as a CCD at a tip of the scope exceeds a dynamic range of the imaging device. Presence of halation causes the image displayed on a monitor to become hard to observe. In addition, halation tends to occur in a region of interest due to an inevitable manner of observation resulting from a shape of the observation target and a structure of the scope, which affects observation and diagnosis.

For example, the inner wall near the stomach entrance is a region of interest where inflammations, such as an ulcer, tend to be observed. When the inner wall is observed, the endoscope apparatus is generally inserted from the entrance and a tip of the scope is bent to turn toward the entrance for observation. At this time, halation tends to occur on the upper or lower side of the inner wall close to the illumination of the scope. Therefore, to observe of the entire stomach entrance, the scope is moved to be twisted with the tip thereof being bent in order to prevent halation from occurring at a part to be observed, since the direction of the tip cannot be freely changed due to the shape of the stomach and a limit resulting from the structure of the scope. Alternatively, a distance between the part to be observed and the scope is changed frequently to adjust illuminance. However, such frequent movement of the scope increases a burden on a patient to be examined, which is not preferable.

For this reason, methods have been proposed in U.S. Pat. No. 6,545,703 and Japanese Unexamined Patent Publications Nos. 2003-250761 and 6(1994)-078312, for example, to reduce halation that causes adverse effects on diagnosis. In these methods, presence of halation is automatically detected based on an average luminance value, a density histogram, or the like of an image obtained by a CCD, and the amount of light is reduced by controlling an iris installed on a light emission side of an illuminating means in the case of presence of halation.

However, according to the methods wherein the amount of light is simply reduced at the time of occurrence of halation, a part where the light cannot easily reach becomes darker and becomes hard to observe, although halation can be suppressed. As a result, the distance between an observation target and a scope, or the illuminance of the light, needs to be adjusted manually from time to time. Consequently, the frequent movement of the scope becomes a burden on a patient, and an operator is troubled with the adjustment of the illuminance.

Therefore, an image obtained by an electronic endoscope apparatus becomes preferable when the image covers a wide range that can be observed at once. In other words, an image with suppressed halation and fewer dark areas is preferable. If such an image is obtained, the burden on a patient and the trouble of illuminance adjustment can be reduced.

SUMMARY OF THE INVENTION

The present invention has been conceived based on consideration of the above circumstances. An object of the present invention is therefore to provide an electronic endoscope apparatus that enables acquisition of an image with suppressed halation and fewer dark areas.

Meanwhile, a method has generally been known for adjusting a luminance level by carrying out gamma processing on a signal obtained by a CCD after decreasing illuminance in the case where halation has been detected. In this method, gamma processing is carried out on a signal obtained by a CCD of a scope by using a gamma value having an inverse characteristic to a non-linear characteristic between a signal and luminance of an image display device, in order to obtain an image having luminance that is linear to the obtained signal. In this manner, a component having the non-linear characteristic is canceled out. This method is therefore completely different from the present invention. The gamma processing described above changes luminance of the signal at all luminance levels to one direction (that is, to higher levels). Therefore, if the gamma processing is applied to a signal obtained by a CCD, a signal having luminance of an intermediate level, whose conversion is not desired, is changed and a part wherein halation is observed is converted to higher luminance. Therefore, such an application cannot achieve the object of the present invention.

An electronic endoscope apparatus of the present invention is an electronic endoscope apparatus comprising a scope having an imaging device for imaging an observation target and illumination means for illuminating the observation target. The electronic endoscope apparatus of the present invention comprises:

halation detection means for detecting halation of a predetermined level or higher occurring in an image represented by an image signal obtained by the imaging device, based on the image signal;

light amount adjustment means for reducing an amount of light emitted from the illumination means so as to cause the halation to become a predetermined level or lower according to detection of the halation by the halation detection means; and luminance conversion means for processing the image signal so that the image represented by the image signal becomes a luminance conversion image wherein only a dark area having a predetermined luminance or lower in the image caused by reduction in the amount of the light has been converted to have a higher luminance.

The halation of the predetermined level or higher may refer to halation occupying a predetermined ratio or more in the image represented by the image signal obtained by the imaging device, for example.

Likewise, the halation of the predetermined level or lower may refer to halation occupying a predetermined ratio or less in the image represented by the image signal obtained by the imaging device.

The predetermined level in the "halation of the predetermined level or higher" is not necessarily the same as the predetermined level in the "halation of the predetermined level or lower".

In the electronic endoscope apparatus of the present invention, the luminance conversion means may generate a blurry image representing a low frequency component of the original image represented by the image signal, based on the image signal. In this case, the luminance conversion means obtains a non-linear conversion image by converting a part exceeding a predetermined luminance in the blurry image to have zero luminance and by converting a part having the predetermined luminance or lower to have a converted luminance corresponding to the original luminance. The luminance conversion means obtains the luminance conversion image by adding the non-linear conversion image to the original image.

In this case, in the conversion to the converted luminance in the blurry image, the part having the predetermined luminance or lower in the blurry image may be converted in such a manner that the lower the luminance of the part is than the predetermined luminance, the higher the luminance of the part becomes after the conversion.

An image luminance control method of the present invention for an electronic endoscope apparatus is a method for controlling image luminance for an electronic endoscope apparatus comprising illumination means for illuminating an observation target and a scope having an imaging device for imaging the observation target. The image luminance control method of the present invention comprises:

a halation detection step wherein halation of a predetermined level or higher occurring in an image represented by an image signal obtained by the imaging device is detected based on the image signal;

a light amount adjustment step wherein an amount of light emitted from the illumination means is reduced so as to cause the halation to become a predetermined level or lower according to detection of the halation in the halation detection step; and a luminance conversion step wherein the image signal is processed so that the image represented by the image signal becomes a luminance conversion image wherein only a dark area having a predetermined luminance or lower in the image caused by reduction in the amount of the light has been converted to have a higher luminance.

In the image luminance control method of the present invention for the electronic endoscope apparatus, the luminance conversion step may comprise the steps of generating from the image signal a blurry image representing a low frequency component of the original image represented by the image signal, obtaining a non-linear conversion image by converting a part exceeding a predetermined luminance in the blurry image to have zero luminance and by converting a part having the predetermined luminance or lower to have a converted luminance corresponding to the original luminance, and obtaining the luminance conversion image by adding the non-linear conversion image to the original image.

In this case, in the conversion to the converted luminance in the blurry image, the part having the predetermined luminance or lower in the blurry image may be converted in such a manner that the lower the luminance of the part is than the predetermined luminance the higher the luminance of the part becomes after the conversion.

According to the electronic endoscope apparatus of the present invention, the halation detection means detects the halation of the predetermined level or higher in the image represented by the image signal obtained by the imaging device, and the light amount adjustment means reduces the amount of the light emitted from the illumination means in order to cause the halation to become the predetermined level or lower. The luminance conversion means then processes the image signal so that the image represented by the image signal becomes the luminance conversion image wherein only the dark area having the predetermined luminance or lower due to decrease in the amount of the light in the image has been converted to have the higher luminance. Therefore, the part in which the halation is observed and image information is thus lost can be changed to have the image information due to the decrease in the amount of the light. In addition, the dark area of the predetermined luminance or lower, which is not easy to see due to the decrease in the amount of the light, can be corrected to become brighter by the luminance conversion. In this manner, the image appropriate for observation can be obtained with reduced halation and fewer dark areas.

BRIEF DESCRIPTION OF THE DRAWINGS

FIG. 2 is a look-up table used for luminance conversion in hypertone processing for obtaining a non-linear conversion image from a blurry image; and FIGS. 3A to 3C show relationships between an amount of light received by a CCD and strength of a video signal.

DESCRIPTION OF THE PREFERRED EMBODIMENT

Figure 1:
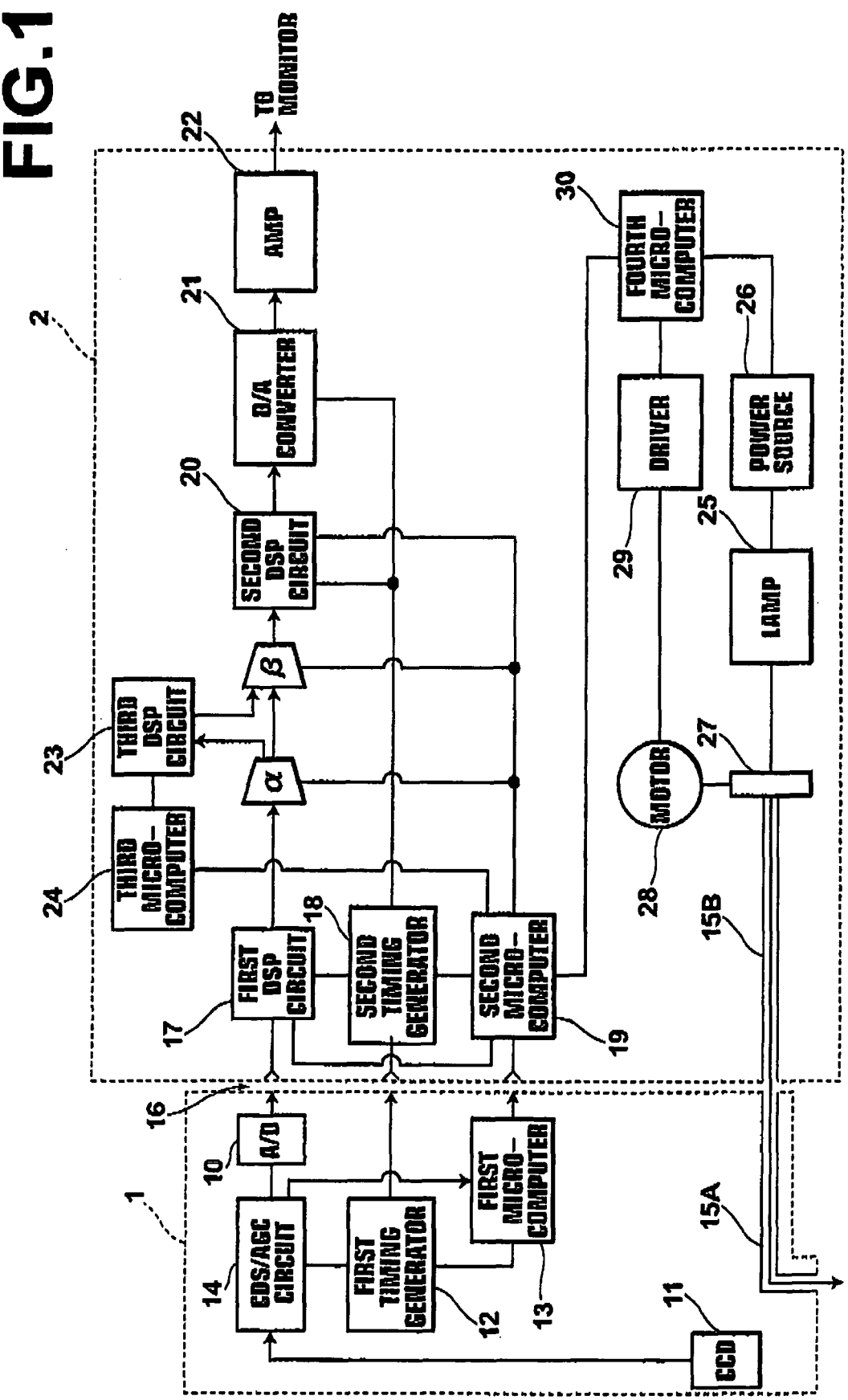
FIG. 1 is a block diagram showing the configuration of an electronic endoscope apparatus of an embodiment of the present invention.

Hereinafter, an embodiment of the present invention will be described.

FIG. 1 shows the configuration of an electronic endoscope apparatus of the embodiment of the present invention. The electronic endoscope apparatus comprises a scope 1 for mainly imaging an observation target and a processor 2 that is connected to the scope 1 and mainly generates a signal for monitor display by processing a signal obtained by the scope 1.

The scope 1 comprises a CCD (an imaging device) 11 installed at a tip thereof, a first timing generator 12 for generating and outputting various kinds of timing signals for the scope 1 including a driving signal for the CCD 11, a first microcomputer 13 for controlling various circuits in the scope 1, a correlated double sampling/automatic gain control (CDS/AGC) circuit 14 for carrying out correlated double sampling and automatic gain control on an image signal as an analog electric signal output from the CCD 11, an A/D converter 10 for converting the signal into a digital signal, and a light guide 15A connected to a light guide 15B in the processor 2 that will be described later for leading light emitted from a lamp 25 to the tip of the scope 1.

The processor 2 comprises a first DSP (Digital Signal Processor) circuit 17, a second timing generator 18, a second microcomputer 19, a second DSP circuit 20, a D/A converter 21, an amplifier 22, a third DSP circuit 23, a third microcomputer 24, the lamp 25, a power source 26 for the lamp 25, an iris 27, a motor 28, a driver 29, a fourth microcomputer 30, and the light guide 15B. The first DSP circuit 17 generates a video signal such as a Y (luminance) signal and a C (color difference) signal, based on the signal sent from the CDS/AGC circuit 14. The first DSP circuit 17 also carries out various kinds of processing on the video signal for generating a color image. The second timing generator 18 synchronizes with the first timing generator 12 for generating and outputting various kinds of timing signals for the processor 2 including a driving signal for the first DSP circuit 17. The second microcomputer 19 receives information on the scope 1 from the first microcomputer 13, and controls the circuits in the processor 2 based on the information. The second DSP circuit 20 generates R (Red), G (Green), and B (Blue) signals for an RGB monitor, based on the Y signal and the C signal sent from the first DSP circuit 17. The D/A converter 21 converts the RGB signals to an analog signal for the monitor, The amplifier 22 amplifies the analog signal for the monitor. The third DSP circuit 23 carries out hypertone processing (proposed by Fuji Photo Film Co., Ltd.) for locally enhancing luminance of a dark area having a predetermined luminance value or lower in the image represented by the signal obtained by the first DSP circuit 17. The third microcomputer 24 controls the third DSP circuit 23. The lamp 25 emits the light to the observation target. The iris 27 is located on a light emission side of the lamp 25. The motor 28 opens and closes the iris 27. The driver 29 drives and controls the motor 28. The fourth microcomputer 30 controls the power source 26 and the driver 29. The light guide 15B is connected to the light guide 15A of the scope 1 for leading the light emitted from the lamp 25 to the scope 1.

Switches α and β are also located between the first DSP circuit 17 and the second DSP circuit 20 for switching a path of the signal. By controlling the switches α and β, selection can be made on whether or not the signal is sent from the first DSP circuit 17 to the second DSP circuit 20 via the third DSP circuit 23. In other words, selection can be made on whether or not the hypertone processing is carried out on the signal.

The scope 1 and the processor 2 are connected to each other by a connector 16 so that the signal obtained by the CCD 11 and control signals are conveyed between the scope 1 and the processor 2.

Each of the circuits is powered by a power supply circuit that is not shown, and the power supply circuit is connected to a commercial power source.

In the configuration described above, the second microcomputer 19 acts as the halation detection means of the present invention, and the fourth microcomputer 30, the driver 29, the motor 28, and the iris 27 act as the light amount adjustment means. The third microcomputer 24 and the third DSP circuit 23 also act as the luminance conversion means of the present invention while the lamp 25 and the light guides 15A and 15B act as the illumination means.

The hypertone processing described above adopts compression processing of an expressible density range, as has been proposed in Japanese Unexamined Patent Publication No. 9(1997)-018704, for example. In the hypertone processing, a blurry image is generated from the signal obtained by the CCD 11, for representing a low-frequency component in an original image represented by the signal. A non-linear conversion image is then obtained by converting a part of the blurry image whose luminance exceeds a predetermined luminance value into a part of zero luminance while converting a part whose luminance is the predetermined luminance value or lower into a part having a converted luminance value. The non-linear conversion image is added to the original image for obtaining an image wherein a dark area has been converted into an area of higher luminance. In this embodiment, the conversion into the converted luminance value is to convert the part whose luminance is the predetermined luminance value or lower in the blurry image into the part of higher luminance in such a manner that the luminance of the part will become higher as the luminance thereof is lower than the predetermined luminance value. For example, this conversion is carried out according to a look-up table (LUT) shown in FIG. 2.

Operation of the electronic endoscope apparatus will be described below.

When the electronic endoscope apparatus is turned on, power is supplied from the power supply circuit to the circuits therein. The driving signal output from the first timing generator 12 drives the CCD 11, and the CCD 11 images the observation target. The image signal is sent to the CDS/AGC circuit 14. The CDS/AGC circuit 14 carries out correlated double sampling on the signal while amplifying the signal with a predetermined gain, and outputs the signal as the video signal to the first DSP circuit 17.

The video signal output from the CDS/AGC circuit 14 is subjected to predetermined processing by the first DSP circuit 17, and sent directly to the second DSP circuit 20, or sent to the second DSP circuit 20 via the third DSP circuit 23. The third DSP circuit 23 carries out the hypertone processing on the signal sent thereto. The second DSP circuit 20 further carries out various kinds of processing on the signal that has been sent thereto, and the video signal for the monitor is output via the D/A converter 21 and the amplifier 22. A video of the observation target is then displayed on the monitor, based on the video signal. The second microcomputer 19 selects whether or not the signal is sent via the third DSP circuit 23, by controlling the switches α and β. In this embodiment, the switches α and β are set so as to cause the signal output from the first DSP circuit 17 to be sent via the third DSP circuit 23 whereby the video signal is always subjected to the hypertone processing. The third microcomputer 24 controls a degree of the hypertone processing upon necessity.

The fourth microcomputer 30 sends a control signal to the driver 29 for causing an amount of the light to the observation target to become a predetermined amount. The driver 29 receives the control signal, and drives the motor 28 for changing opening of the iris 27. In this manner, the light emitted from the lamp 25 is narrowed to the predetermined amount by the iris 27, and emitted to the observation target from the tip of the scope 1 via the light guides 15A and 15B.

The first microcomputer 13 receives the video signal obtained by the CCD 11 from the CDS/AGC circuit 14, and converts the video signal into the digital signal by using the A/D converter 10. The first microcomputer 13 then sends the digital signal to the first DSP circuit 17. The first DSP circuit 17 sends luminance information or the like of the received signal to the second microcomputer 19, and the second microcomputer 19 detects halation by judging whether a part having a predetermined luminance value or higher in the image occupies a predetermined ratio or more in the image, based on the luminance information. The second microcomputer 19 sends a control signal to the fourth microcomputer 30 so as to decrease the amount of the light to the observation target, in response to detection of halation. In the case where the halation exceeding the predetermined level described above has not been detected, the second microcomputer 19 sends a control signal to the fourth microcomputer 30 so as to maintain or increase the amount of the light to the observation target. In the case where the halation of the predetermined level or higher has been detected, the second microcomputer 19 sends the control signal to the fourth microcomputer 30 for decreasing the amount of the light to the observation target so that the halation becomes a predetermined level or lower, resulting in the part of the halation occupying a predetermined ratio or less in the image. The second microcomputer 19 sends light control information to the third microcomputer 24 for representing adjustment of the amount of the light. The fourth microcomputer 30 sends the control signal to the driver 29 for controlling the motor 28, according to the control signal sent thereto. The driver 29 drives the motor 28 for controlling opening of the iris 27. Meanwhile, the third microcomputer 24 controls the third DSP circuit 23, based on the light control information. More specifically, the third microcomputer 24 controls the third DSP circuit 23 so that the hypertone processing by the third DSP circuit 23 is strengthened more as the amount of the light to the observation target decreases more. In other words, the signal representing the predetermined dark area is converted to represent a signal of higher luminance while the hypertone processing is controlled to the same degree as in the case of not carrying out the hypertone processing if the amount of the light is the same as the amount of the light that has been set originally.

Generally speaking, a relationship between the amount of the light received by the CCD 11 and strength of the video signal can be shown by a broken line in FIG. 3A. However, in presence of halation, a range of the amount of the light received by each of pixels in the CCD 11 and the strength of the video signal is shown by solid lines a. In other words, the strength of the video signal is saturated for the amount of the light of a predetermined level or higher, meaning that image information corresponding to pixels receiving the light in this range is lost. If the amount of the light to the observation target is decreased, the range of the amount of the light received by each of pixels in the CCD 11 and the strength of the video signal is shown by a solid line b in FIG. 3B. Therefore, although the strength of the video signal decreases as a whole, the image information can be maintained over the entire range of the received light. However, a part that was originally dark becomes darker as a result of the decrease in the amount of the light, causing the part to become hard to see in the displayed image. For this reason, by carrying out the processing such as the hypertone processing on the video signal obtained by the CCD 11 for converting only the dark area whose luminance is in the predetermined range lower than a predetermined level in the image represented by the video signal into the area of higher luminance (that is, by carrying out processing for enhancing the signal strength), the relationship between the amount of the light received by each of the pixels in the CCD 11 and the strength of the video signal can be shown by solid lines c in FIG. 3C. In this manner, the image appropriate for observation can be obtained with suppressed halation and fewer dark areas. Note that in FIGS. 3A, 3B, and 3C, X indicates saturation strengths of the video signal.

As has been described above, according to the electronic endoscope apparatus in this embodiment, the second microcomputer 21 as the halation detection means detects halation of the predetermined level or higher in the image represented by the image signal obtained by the CCD 11 as the imaging device, and the fourth microcomputer 30, the driver 29, the motor 28, and the iris 27 as the light amount adjustment means decrease the amount of the light from the lamp 25 and the light guides 15A and 15B as the illumination means so as to suppress the halation to the predetermined level or lower. The third microcomputer 24 and the third DSP circuit 23 as the luminance conversion means processes the image signal so that only the dark area having the predetermined luminance value or lower in the image represented by the image signal due to the decrease in the amount of the light can be converted to have higher luminance. Therefore, the part of the halation wherein the image information is lost can be changed to a part having the image information by the decrease in the amount of the light while the predetermined dark area that is not easy to see due to the decrease in the amount of the light can be corrected to have higher luminance by the luminance conversion. In this manner, the image having suppressed halation and fewer dark areas can be obtained, which is appropriate for observation.

The processing for converting the dark area having the predetermined luminance value or lower into the part of higher luminance is not necessarily limited to the hypertone processing described above. For enhancing the signal of the dark area may also be used a method of gradation conversion by using a one-dimensional look-up table (1D-LUT) or a method of controlling the gain of the CCD 11 by the CDS/AGC circuit 14.

The CCD 11 is either a primary-color CCD or a complementary-color CCD.

The range for luminance enhancement and the degree of enhancement by the hypertone processing or the like may be set freely upon necessity, according to a purpose of observation or use of the image, for example.

What is claimed is:

1. An electronic endoscope apparatus comprising a scope having an imaging device for imaging an observation target and illumination means for illuminating the observation target, the electronic endoscope apparatus comprising:

halation detection means for detecting halation of a predetermined level or higher occurring in an image represented by an image signal obtained by the imaging device, based on the image signal;

light amount adjustment means for reducing an amount of light emitted from the illumination means so as to cause the halation to become a predetermined level or lower according to detection of the halation by the halation detection means; and luminance conversion means for processing the image signal so that the image represented by the image signal becomes a luminance conversion image, wherein only a dark area having a predetermined luminance or lower in the image caused by reduction in the amount of the light has been converted to have a higher luminance, and wherein the luminance conversion means generates from the image signal a blurry image representing a low frequency component of the original image represented by the image signal, obtains a non-linear conversion image by carrying out conversion of luminance of a part exceeding a predetermined luminance in the blurry image into zero luminance and by carrying out conversion of luminance of a part having the predetermined luminance or lower into a converted luminance corresponding to the original luminance, and obtains the luminance conversion image by adding the non-linear conversion image to the original image.

2. The electronic endoscope apparatus according to claim 1, wherein the conversion into the converted luminance in the blurry image is conversion of the part having the predetermined luminance or lower in the blurry image in such a mariner that the lower the luminance of the part is than the predetermined luminance the higher the luminance of the part becomes after the conversion.

3. An image luminance control method for an electronic endoscope apparatus comprising illumination means for illuminating an observation target and a scope having an imaging device for imaging the observation target, the image luminance control method comprising the steps of:

detecting halation of a predetermined level or higher occurring in an image represented by an image signal obtained by the imaging device, based on the image signal;

reducing an amount of light emitted from the illumination means so as to cause the halation to become a predetermined level or lower according to detection of the halation; and processing the image signal so that the image represented by the image signal becomes a luminance conversion image, wherein only a dark area having a predetermined luminance or lower in the image caused by reduction in the amount of the light has been converted to have a higher luminance, and wherein the step of processing the image signal comprises the steps of generating from the image signal a blurry image representing a low frequency component of the original image represented by the image signal, obtaining a non-linear conversion image by carrying out conversion of luminance of a part exceeding a predetermined luminance in the blurry image into zero luminance and by carrying out conversion of luminance of a part having the predetermined luminance or lower into a converted luminance corresponding to the original luminance, and obtaining the luminance conversion image by adding the non-linear conversion image to the original image.

4. The image luminance control method for the electronic endoscope apparatus according to claim 3, wherein the conversion into the converted luminance in the blurry image is conversion of the part having the predetermined luminance or lower in the blurry image in such a manner that the lower the luminance of the part is than the predetermined luminance the higher the luminance of the part becomes after the conversion.

* * * * *